United States Patent [19]

Brunetti et al.

[11] Patent Number: 4,874,844

[45] Date of Patent: Oct. 17, 1989

[54] TRIPEPTIDE WITH IMMUNOSTIMULATING ACTIVITY

[75] Inventors: Brunetto Brunetti, Milan; Marco Prada, Casalpusterlengo, both of Italy

[73] Assignee: Ellem Industria Farmaceutica S.p.A., Milan, Italy

[21] Appl. No.: 35,045

[22] Filed: Apr. 6, 1987

[30] Foreign Application Priority Data

Apr. 9, 1986 [IT] Italy ............................. 20026 A/86

[51] Int. Cl.$^4$ ............................................. C07K 5/08
[52] U.S. Cl. ..................................... 530/331; 514/18; 424/85.1
[58] Field of Search .......................... 530/331; 514/18; 424/85.1

[56] References Cited

U.S. PATENT DOCUMENTS 4,428,938 1/1984 Kisfaludy ............................. 530/331

OTHER PUBLICATIONS

Diezel et al, Biomed. Biochim. Acta vol. 45(10) pp. 1349–1352 (1986).
Rudinger, Peptide Hormones, Parsons (Ed.) U Park Press Baltimore, pp. 1–7, (1976).
Fanci; PNAS vol-83 pp. 9278–9283 (12/86).
Lewis, A. J. et al., Ann. Rep. Med. Chem.—17, 191–202 (1982).
Talmadge, J. E. et al., 13th Int. Cong. of Chemotherapy, Vienna 28/8–2/9/1983, SY 64—part 203, p. 19.
Hadden et al., Advances in Immunopharmacology 3 (1985).
Lesourd, B. M. et al., Int. J. Immunopharmacol.—10, 135 (1988).
Masihi K. N. et al., Nat. Immun. Cell Growth Regul., 6:213–218 (1987).
Gilman and Lewis, Drug Discovery and Development, Williams M., Malick, J. b., eds, Humana Press (1987) p. 227.
Experienta—42, 521, 1986.
Hadden, J. W. —J.A.M.A.—258, 3005, 1987.
Trainin et al., Immunol. Today, 4, 16–21 (1983).
Doria and Frasca, "Tumor Immunology and Immunoregulation by Thymic Hormones", Dammacco F., Ed., Masson (1987) pp. 109–219.
Sztein and Goldstein, Springer Semin. Immunopathol. (1986) 9:1–18.
Schulof and Goldstein, Rec. Adv. Clin. Immunol. 3, 243–286 (1983).
Schulof et al., Drugs Fut. 11, 783, (1986).
Goldstein et al., Med. Oncol. & Tumor Pharmacother., 3, 211–221 (1986).
Immunopharmacology, 16, 97–105 (1988).
Burstein Y. et al., Biochemistry, 27, 4066–4071 (1988).
Waymack et al, Surgery, 96, 308–314 (1984).
Meroni et al., Clin. Immunol. & Immunopathol., 42, 151–159 (1987).
Barcellini et al., Clin. Exp. Immunol., 67, 537–543 (1987).
Pipino and Vittore, Arznei. Forsch./Drug Res. 38(I), 116–119 (1988).
Munno et al., Cytobios, 52, 167–173 (1987).

*Primary Examiner*—Delbert R. Phillips
*Assistant Examiner*—Christina Chan
*Attorney, Agent, or Firm*—Ladas & Parry

[57] ABSTRACT

The tripeptide Arg-Lys-Glu, synthetized by conventional solution methods, and its salts display immunostimulating activity both on maturation of immature T cells and on T cell function.

3 Claims, 1 Drawing Sheet

TRIPEPTIDE WITH IMMUNOSTIMULATING ACTIVITY

BACKGROUND OF THE INVENTION

The invention describes the synthesis and chemical and immunopharmacological characteristics of the tripeptide Arg-Lys-Glu.

SUMMARY OF THE INVENTION

Arg-Lys-Glu is able to stimulate both in vitro and in vivo, the maturation of immature lymphocytes, and in vitro the function of T cells. In fact, it stimulates the maturation of immature murine T cells both in vitro and in vivo, and in vitro induces lymphokine production, activation (RNA synthesis) and profileration (DNA synthesis) in human T cells, besides being devoid of any toxicity or severe side-effects when administered to mice.

DETAILED DESCRIPTION OF THE INVENTION

Chemical Characteristics

Figure 1:
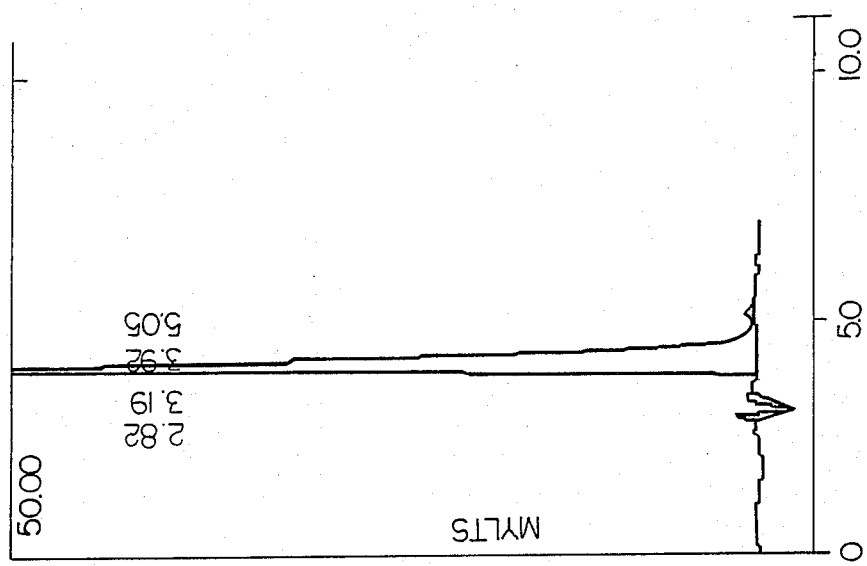
FIG. 1 is the HPLC profile of the tripeptide Arg-Lys-Glu obtained according to the method described in example 1.

Molecular weight: 431.52.
Optical Rotation: $[\alpha]_D^{20} = 5.13$. (c=1, acetic acid).
HPLC analysis:
The tripeptide has been analyzed by means of ion-pairing HPLC, according to the separation conditions here described:
Eluent: $NaH_2P_4$ 0.05M pH 4.3+SDS $5\times10^{-4}$M, MeOH; 50:50.
Flow rate: 1 ml/min.
Detection: 225 nm.
Injection volume: 20 mcl.
Sample: 20 mcg.
Column: u Bondapack C18 (waters), 300×3.9 mm.
The following instrumentation was used:
Liquid chromatograph: SERIES 4 (Perkin Elmer).
Injection valve: Reodyne mod. 7125-075, with a 20 ul loop.
Detector: Spectrophometer LC 95 (Perkin Elmer).
Computing integrator: Data Station 3600 (Perkin Elmer).
The figure shows the HPLC profile of the tripeptide.

Resistance to the In Vitro Simulated Gastric Ambient

The tripeptide is resistant to the in vitro simulated gastric ambient. In this study the gastric simulated juice USP XXI (HCl+pepsin) has been used at 37 C for 5 hrs.

SYNTHESIS

εZ(Cl)εOBe Boc-Lys-Glu-εOBe (1)

εZ(Cl)
Boc-Lys (0.1 mole) dissolved in methylene chloride and cooled to 0 C was added to N-Methylmorpholine (0.1 mole). The solution was cooled to −15 C +/−1 isobutyl chloroformate (0.1 mole) was added under stirring while maintaining the temperature at −15 C. After stirring the reaction mixture for 15 minutes at this temperature, a precooled solution of glutamic acid-dibenzyl ester-p-tosylate (0.1 mole) and N-methylmorpholine (NMM) (0.1 mole) in dimethyl formamide was added slowly and the reaction mixture stirred overnight. Solvents were removed under reduced pressure and the residue was taken up in ethyl acetate. The ethyl acetate was washed with water, 1N-hydrochloric acid, water 5% sodium bicarbonate solution and water. It was dried over sodium sulphate and solvent removed under reduced pressure. The product is syrup. TLC System CHC13:MeOH:HOAc (90:8:2). 95% pure: Yield 80%.

(1) was deblocked with 50% trifluoro acetic acid-methylene chloride mixture (1:1), 10 ml per gram, for half and hour. It was evaporated under reduced pressure, triturated with ether, filtered, washed with ether and dried in vacuo.

Yield 98%. ypsilon Z(Cl)ypsilon OBe The TFA-Lys-Glu-OBe was neutralized with NMM and coupled to Z3-Arg in dimethyl formamide-tetra-hydrofuran mixture using NMM and isobutyl chloroformate and worked up as in (1).

Yield 60%. TLC System CHC13:MeOH (92:8). One major spot.

The above tripeptide was hydrogenated in acetic acid-water methanol mixture in presence of pd/c until its completion. It was filtered from catalyst and the filtrate was evaporated in vacuo.

The product, tripeptide, was purified by counter current distribution using system N-butanol: acetic acid: water (4:1:5) Yield 50%. TLC System butanol: acetic acid: water: pyridine (32:6:22:20). One major spot. HPLC 97%.

BIOLOGICAL ACTIVITIES

1.A. In vitro induction of thy 1.2 antigen

The capacity of Arg-Lys-Glu (hereinafter referred to as "ELS1") to induce in vitro the differentiation of mouse T cell precursors into lymphocytes expressing T cell markers has been tested by evidencing the induction of Thy 1.2 membrane antigen.

MATERIAL AND METHODS

Mice: 8 week-old athymic (nu/nu) mice outbred on C3H/He background, maintained under specific pathogen-free conditions were used.

Preparation of the cells: mice were killed by cervical dislocation. Spleens were aseptically removed and finely minced with forceps in Hank's balanced salt solution (HBSS) (Gibco Ltd, Paisley, Scotland). Splenocytes, washed and resuspended in 199 medium (Gibco Ltd) supplemented with 1% BSA (Boehringer Mannheim) and gentamycin (100 ug/ml) were incubated for 45 minutes in equilibrated nylon wool columns according to the method of Julius et al. (Eur. J. Immunol. 3, 645, 1973). The effluent cell populations enriched with precursor T cells, were used in the bioassay.

Induction bioassay: $0.5\times10^6$ effluent cells in 0.1 ml medium were incubated at 37 C. for 18 hours with 0.1 ml of tripeptide or medium alone. Cultures were done in duplicate. At the end of the incubation, the cells were washed with 0.87% ammonium chloride to lyse red cells and then with HBSS. The induction of membrane Thy 1.2 antigen was determined by a direct immunofluorescence test.

Direct immunofluorescence: the cells were incubated at 4 C for 20 minutes with fluorescein-conjugated monoclonal antibody (Bio-Yeda) at 1:200 dilution. The mixture was centrifuged at 300 g for 5 minutes, washed twice in HBSS and then suspended for counting at the fluorescence microscope (Leitz Orthoplan). The difference in percentages of fluorescing cells between cultures with and without tripeptide gave the inducing activity of the product.

RESULTS

As shown in the table, the tripeptide induces the appearance of the marker Thy 1.2 on immature T cells with an optimum response at 1 mcg/ml. The dose-response relationship curve is bell-shaped, as both lower and higher concentrations of the peptide provoke a smaller induction.

| PEPTIDE CONCENTRATION (mcg/ml) | % THY 1.2+CELLS MEAN +/− S.E. | DIFFERENCE |
|---|---|---|
| 0 | 11 +/− 1.6 | — |
| 0.0001 | 19 +/− 1.2 | +8 |
| 0.001 | 34 +/− 3.3 | +23 |
| 0.01 | 44 +/− 3.1 | +33 |
| 0.1 | 50 +/− 1.2 | +39 |
| 1 | 54 +/− 5.0 | +43 |
| 10 | 45 +/− 4.9 | +34 |
| 20 | 40 +/− 1.2 | +29 |
| 50 | 28 +/− 4.5 | +17 |
| 100 | 21 +/− 1.7 | +10 |
| 200 | 16 +/− 2.4 | +5 |

1.B In vivo induction of thy 1.2 antigen

ELS1 was administered on 4 consecutive days after which the mice were rested for 24 hrs. and then the spleens were removed and cells were examined for expression of the Thy 1.2 antigen by fluorescence. The control mice were given Medium 199 (M 199), the medium in which the drug was dissolved. The mice had an average weight of about 24 g.

RESULTS

| | % THY 1.2+ CELLS | |
|---|---|---|
| | Oral | i.p. |
| Control | 3% | 5% |
| ELS1 42 ug/kg | 3% | 6% |
| ELS1 420 ug/kg | 5% | 8% |
| ELS1 1055 ug/kg | 7% | 12% |
| ELS1 2110 ug/kg | 15% | 18% |
| ELS1 4220 ug/kg | 14% | 17% |
| ELS1 8440 ug/kg | 15% | 16% |

The data show that ELS1 is able to induce the maturation of splenocytes after both oral and i.p. administration.

The optimal dosage is 2110 ug/kg while with higher dosages a plateau response is observed.

2. In vitro stimulation of lymphokine production
Material and methods
Preparation of human peripheral blood mononuclear cells (PBMC).

Peripheral blood is obtained from healthy volunteers by venipuncture. The red blood cells are separated from white cells on Ficoll-Hipaque gradients. The buffy coat (PBMC) is removed and washed, and the cells are resuspended at $1 \times 10^6$ cells/ml in RPMI 1640, supplemented with 1% penicillin/streptomycin, 1% glutamine and 1% heat inactivated fetal calf serum (FCS, 56 C 30 min).

Preparation of growth factor PBMC at $1 \times 10^6$ cells/ml in 1% heat inactivated FCS are incubated with or without Phytohemmagglutinin (PHA) at 0.75% concentration v/v. The peptide to be tested is added at the concentration of 1 ug/ml to appropriate cultures. The incubation period is 18–24 hrs., at 37 C in a humidified atmosphere. The cultures are then filtered through 0.22 mM filters and supernatants are examined for the presence of growth factors.

Measurement of growth factors in supernatants
A. Test cells

The B cells used to test for the presence of B cell growth factor (BCGF) are long term cultured cell lines, maintained on BCGF, and are EBV negative. These cells are grown in serum free medium using Nutridoma (Boehringer Mannheim Biochemicals), and do not respond to IL-2.

The T cells used to test for the presence of IL-2 are freshly isolated. They are initially stimulated with PHA (0.75%) and are maintained in culture for at least 10 days prior to use (to reduce background and establish their dependence on IL-2).

B. Preparation of Test cells for Use in Assay.

1. B cells are usually used 4 days after the last feeding with BCGF. They are washed 4 times in EPMI 1640 to remove any remaining BCGF, and adjusted to $15 \times 10^4$ cells/ml in RPMI 1640 and Nutridoma (at 1% final concentration).

2. T cells are used 4 days after the last feeding with IL-2. They are washed $4\times$ and adjusted to $50 \times 10^4$ cells/ml in RPMI 1640 with 5% FCS.

C. Assay Procedures

1. Long term cultured B cells are incubated with various concentrations of supernatant from PBMC cultures, in 96 flat bottom microtiter plates. Each well has a total volume of 200 ul, consisting of 100 ul of B cells ($15 \times 10^3$ cells) and 100 ul of supernatant. We examine the efficacy of our test B cells by incubating them with various concentrations of purified BCGF (Cellular Products, Inc. Buffalo, N.Y.).

The cultures are incubated for 24 hrs., after which 1 uCi of [$^3$H-Tdr] is added and then incubated additionally for 12 hrs. The cultures are then harvested and counted in a scintillation counter.

2. T cells are incubated in flat bottom wells. The total volume in each well is 200 ul, which includes $50 \times 10^3$ T cells/well. The incubation period is 72 hrs which includes 12 hrs of labelling with [$^3$H-Tdr].

RESULTS

| (1) GROWTH FACTOR PRODUCTION | | | | | |
|---|---|---|---|---|---|
| EXPERIMENT 1 | | | | | |
| BCGF ACTIVITY (C.P.M.) | | | | | |
| | % Sup. | | | | |
| Supt. from | 3.05 | 6.25 | 12.5 | 25 | 50 |
| PBL + PHA | 424 | 1026 | 1674 | 3172 | 8392 |
| PBL + PHA + ELS1 | 684 | 1658 | 2863 | 5600 | 7838 |
| TCGF ACTIVITY (C.P.M.) | | | | | |
| | % Sup. | | | | |
| PBL + PHA | 542 | 192 | 224 | 564 | 1144 |
| PBL + PHA + ELS1 | 624 | 438 | 1062 | 1926 | 3296 |
| EXPERIMENT 2 | | | | | |
| BCGF ACTIVITY (C.P.M.) | | | | | |
| | % Sup. | | | | |
| Supt. from | 3.125 | 6.25 | 12.5 | 25 | 50 |
| PBL + PHA | 1369 | 2187 | 2894 | 4876 | 8104 |
| PBL + PHA + ELS1 | 1586 | 2837 | 3994 | 7728 | 10886 |
| TCGF ACTIVITY (C.P.M.) | | | | | |
| | % Sup. | | | | |
| PBL + PHA | 1482 | 3146 | 4322 | 7184 | 9012 |
| PBL + PHA + ELS1 | 1908 | 4424 | 6480 | 9329 | 11656 |

3. Effect on RNA synthesis

Effect of ELS1 on RNA synthesis in human T cells, as observed by incorporation of $^3$H-uridine. Counts per minute (CPM). Results obtained after 24 hrs. of incubation.

T: 3732.

T+PHA: 20752.

|  | ELS1 Concentration ug/ml | | | |
| --- | --- | --- | --- | --- |
|  | 0.1 | 1 | 10 | 20 |
| T + ELS1 | 5336 | 4868 | 5104 | 5272 |
| T + ELS1 + PHA | 32729 | 34966 | 34497 | 31764 |

4. Effect on DNA synthesis

Effect of ELS1 on DNA synthesis in human T cells as observed by incorporation of $^3$H-thymidine. Counts per minute (CPM). Results obtained after 3 days of incubation.

T: 154.

T+PHA: 6076.

|  | ELS1 Concentration ug/ml | | | |
| --- | --- | --- | --- | --- |
|  | 0.01 | 0.1 | 1 | 10 |
| T + ELS1 | 262 | 242 | 196 | 240 |
| T + ELS1 + PHA | 5908 | 6810 | 7264 | 9560 |

5. Vitro increase of cell number

The tripeptide, added to cultures of either T lymphocytes or mixtues of T and B lymphocytes every fourth day at a concentration of 5 ug/ml for period of 30 days, is able to increase cell number with a maximum of +50% with respect to control cultures, observed between day 10 and day 15 of the experiment.

TOXICOLOGICAL STUDIES

Acute Toxicity

Acute toxicity studies carried out on mice and rats have shown that up to a dose of 1000 mg/Kg i.m. the tripeptide is totally devoid of toxic effects.

Tolerability

Studies on rabbits and mice have shown that the product, at the dosage of 100 mg/Kg respectively i.v. and i.p., doesn't cause any hemodynamic modification and behavioral effect. Particularly, pentobarbital-induced sleeping time shows only a slight increase.

Allergy-Inducing Activity

The product, at the dosage of 100 mg/Kg i.m. doesn't induce any sensitization phenomena in the guinea-pig.

SALTS OF THE TRIPEPTIDE

The above mentioned researches have been carried out with an acetate salt of the tripeptide, however it is well known to the state of the art that similar results can be obtained using other salts, for istance trifluoroacetate, hydrochloride, sulfate.

We claim:

1. A tripeptide consisting of L-Arg (arginine), L-Lys (lysine) and L-Glu (glutamic acid) and having the following structure: Arg-Lys-Glu or a pharmaceutically acceptable salt thereof.

2. The tripeptide as in claim 1 wherein the pharmaceutically acceptable salt thereof is selected from the group consisting of the acetate, trifluoroacetate, hydrochloride and sulfate salts.

3. The tripeptide, as in claim 2, wherein the pharmaceutically acceptable salt is the acetate salt.

* * * * *